United States Patent
Djiofack

(10) Patent No.: US 11,717,231 B2
(45) Date of Patent: *Aug. 8, 2023

(54) ULTRASOUND ANALYTICS FOR ACTIONABLE INFORMATION

(71) Applicant: Alarm.com Incorporated, Tysons, VA (US)

(72) Inventor: Innocent Djiofack, Vienna, VA (US)

(73) Assignee: Alarm.com Incorporated, Tysons, VA (US)

( * ) Notice: Subject to any disclaimer, the term of this patent is extended or adjusted under 35 U.S.C. 154(b) by 198 days.

This patent is subject to a terminal disclaimer.

(21) Appl. No.: 17/195,005

(22) Filed: Mar. 8, 2021

(65) Prior Publication Data

US 2021/0287056 A1 Sep. 16, 2021

Related U.S. Application Data

(63) Continuation of application No. 16/205,037, filed on Nov. 29, 2018, now Pat. No. 10,943,153.

(Continued)

(51) Int. Cl.
*A61B 5/00* (2006.01)
*G06T 7/70* (2017.01)
(Continued)

(52) U.S. Cl.
CPC .......... *A61B 5/7267* (2013.01); *A61B 5/1113* (2013.01); *A61B 5/746* (2013.01);
(Continued)

(58) Field of Classification Search
CPC ................ G06K 9/6289; B64C 39/024; B64C 2201/12; B64D 47/02; G06T 7/70;
(Continued)

(56) References Cited

U.S. PATENT DOCUMENTS 8,983,682 B1 3/2015 Peeters et al.
9,456,800 B2 10/2016 Anthony et al.
(Continued)

OTHER PUBLICATIONS

PCT International Search Report and Written Opinion in International Application No. PCT/US2018/063146, dated Mar. 1, 2019, 13 pages.

(Continued)

*Primary Examiner* — Qun Shen
(74) *Attorney, Agent, or Firm* — Fish & Richardson P.C.

(57) ABSTRACT

Systems and techniques are described for gathering information on the health of individuals trapped in an accident to provide actionable information to a first responder system. In some implementations, a monitoring system monitors a property that includes sensors located at the property and generate first sensor data. A monitor control unit receives the first sensor data and generates an alarm event for the property based on the first sensor data. Based on generating the alarm event for the property, the monitor control unit dispatches an autonomous drone. The autonomous drone is configured to navigate the property. Using an onboard sensor, the autonomous drone generates second sensor data. Based on the second sensor data, the autonomous drone determines a location within the property where a person is likely located. The autonomous drone provides, for output, data indicating the location within the property where the person is likely located.

20 Claims, 6 Drawing Sheets

Related U.S. Application Data

(60) Provisional application No. 62/591,920, filed on Nov. 29, 2017.

(51) Int. Cl.
*B64C 39/02* (2023.01)
*G08B 13/22* (2006.01)
*B64D 47/02* (2006.01)
*G08B 21/02* (2006.01)
*A61B 5/11* (2006.01)
*G08B 25/00* (2006.01)
*G01S 15/89* (2006.01)
*G05D 1/00* (2006.01)
*G06V 40/10* (2022.01)
*G06F 18/25* (2023.01)
*B64U 101/00* (2023.01)

(52) U.S. Cl.
CPC ............ *B64C 39/02* (2013.01); *B64C 39/024* (2013.01); *B64D 47/02* (2013.01); *G01S 15/89* (2013.01); *G05D 1/0094* (2013.01); *G06F 18/251* (2023.01); *G06T 7/70* (2017.01); *G06V 40/10* (2022.01); *G08B 13/22* (2013.01); *G08B 21/02* (2013.01); *G08B 25/00* (2013.01); *B64U 2101/00* (2023.01); *G06T 2207/10032* (2013.01); *G06T 2207/20081* (2013.01); *G06T 2207/30196* (2013.01)

(58) Field of Classification Search
CPC . G06T 2207/10032; G06T 2207/20081; G06T 2207/30196
See application file for complete search history.

(56) References Cited

U.S. PATENT DOCUMENTS

| | | |
|---|---|---|
| 11,423,489 B1 * | 8/2022 | Grant ..................... G08G 1/012 |
| 2002/0060267 A1 | 5/2002 | Yavnai |
| 2009/0048500 A1 | 2/2009 | Corn |
| 2014/0278478 A1 | 9/2014 | Vezina |
| 2017/0092109 A1 * | 3/2017 | Trundle ................. G16H 40/20 |
| 2017/0119347 A1 | 5/2017 | Flores, II et al. |
| 2017/0177925 A1 | 6/2017 | Volkart |
| 2018/0029522 A1 | 2/2018 | Gordon et al. |
| 2018/0144615 A1 | 5/2018 | Kinney et al. |
| 2018/0251122 A1 * | 9/2018 | Golston ........... B60W 50/0098 |
| 2019/0014461 A1 | 1/2019 | Winkle et al. |
| 2019/0095687 A1 * | 3/2019 | Shaw ..................... A61B 5/741 |

OTHER PUBLICATIONS

EP Summons to Attend Oral Proceedings in European Appln. No. 18827313.0, dated Jan. 12, 2023, 7 pages.

* cited by examiner

400

```
┌─────────────────────────────────────────────────────────────────────────┐
│ Determine an identification of an individual in a frame of image data   │
│                                                                     402 │
└─────────────────────────────────────────────────────────────────────────┘
                                    │
                                    ▼
┌─────────────────────────────────────────────────────────────────────────┐
│ Determine a location of the identified individual in the frame of data  │
│ using locational coordinates                                            │
│                                                                     404 │
└─────────────────────────────────────────────────────────────────────────┘
                                    │
                                    ▼
┌─────────────────────────────────────────────────────────────────────────┐
│ Obtain ultrasound data of the identified individual in response to a    │
│ drone's movement in proximity to the location of the identified         │
│ individual to capture the ultrasound data                               │
│                                                                     406 │
└─────────────────────────────────────────────────────────────────────────┘
                                    │
                                    ▼
┌─────────────────────────────────────────────────────────────────────────┐
│ Provide the identification of the individual, the location of the       │
│ identified individual, the frame of image data, and the ultrasound data │
│ of the identified individual to a remote processing unit                │
│                                                                     408 │
└─────────────────────────────────────────────────────────────────────────┘
```

```
Obtain an identification of an individual, a location of the identified individual, a
frame of image data, and ultrasound data of the identified individual from a drone
                                                                              502
                                         ↓
Generate an ultrasound image from obtained ultrasound data
                                                         504
                                         ↓
Determine whether the ultrasound image includes the identified individual as having
                              an injury
                                                                              506
                                         ↓
Generate a severity indicator corresponding to each of the ultrasound images
                                                                           508
                                         ↓
Generate a mapped environment that includes the ultrasound images stitched
together that includes the corresponding severity indicator for each of the ultrasound
                              images
                                                                              510
                                         ↓
Provide the mapped environment to a first responder system
                                                         512
```

FIG. 5

ULTRASOUND ANALYTICS FOR ACTIONABLE INFORMATION

CROSS-REFERENCE TO RELATED APPLICATION

This application is a continuation of U.S. application Ser. No. 16/205,037, filed Nov. 29, 2018, which claims the benefit of U.S. Provisional Application No. 62/591,920 filed Nov. 29, 2017, and titled "Ultrasound Analytics for Actionable Information. The complete disclosures of all of the above patent applications are hereby incorporated by reference in their entirety for all purposes.

TECHNICAL FIELD

This specification relates generally to integrated security technology, and in particular, to integrated security technology to provide actionable information to first responders using ultrasound data.

BACKGROUND

Integrated security includes the use of security hardware in place on a property, such as a residential property and a commercial property. Typical uses of security at a particular property includes detecting intrusion, detecting unlocked doors, detecting when an individual is harmed at the property, and tripping one or more alarms.

SUMMARY

The subject matter of the present disclosure is related to systems and techniques for gathering information on the health of one or more individuals trapped in an accident to provide actionable information to a first responder system. The techniques may use ultrasound, camera images, GPS locational data, and machine learning algorithms to provide the actionable information to the first responder system. The machine learning algorithms may include algorithms such as one or more neural network models, Bayesian learning models, or any other type of machine learning technique, to detect injuries of the individuals trapped in the accident. In response to detecting injuries of the individuals trapped in the accident, the systems may transmit a notification to a first responder system and other individuals that may know the injured individual indicating the individual is trapped and injured. The benefit of providing the indication of the injured individual is such that other individuals related to the injured individual can be aware of the status of the injured individual in the case of an emergency, such as a fire, earthquake, or flood, to name a few examples. Additionally, by notifying the first responder system, the first responder system can take one or more steps to save the injured individuals when time is of the essence and the injured individual's life is in severe condition. The one or more steps may include pinpointing the location of the injured individual at a facility that has toppled due to a natural disaster when finding the injured individual is next to impossible with the human eye alone, notifying one or more other individuals of the injured individual's status and location, and determining the injury of the injured individual in an efficient manner to provide the correct care.

In some implementations, the techniques may utilize a set of sensors including a camera (or an array of cameras), a Global Positioning System (GPS) device, and an ultrasound transducer. Each of the sensors may be co-located and mounted on one unit, such as a plane or drone. The sensors can communicate to a backend over a WiFi or cellular communication network. In some implementations, the backend is responsible for transforming the data provided by each of the cameras, the GPS device, and the ultrasound transducer into one or more various types of data and performing advanced analytics on the various types of data. In some implementations, the backend is responsible for aggregating the various types of data into an aggregated map that incorporates all usable information provided by the camera, the GPS device, and the ultrasound transducer. The backend may provide the aggregated map to a first responder system such that the first responder system can identify and prioritize providing actionable rescue teams for the identified individuals.

In one general aspect, a method is performed by one or more computers of a monitoring system. The method includes generating, by one or more sensors of a monitoring system that is configured to monitor a property, first sensor data; based on the first sensor data, generating, by the monitoring system, an alarm event for the property; based on generating the alarm event for the property, dispatching, by the monitoring system, an autonomous drone; navigating, by the autonomous drone of the monitoring system, the property; generating, by the autonomous drone of the monitoring system, second sensor data; based on the second sensor data, determining, by the monitoring system, a location within the property where a person is likely located; and provide, for output by the monitoring system, data indicating the location within the property where the person is likely located.

Other embodiments of this and other aspects of the disclosure include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

Implementations may include one or more of the following features. For example, in some implementations, based on navigating the property, generating, by the monitoring system, a map of the property; and providing, by the monitoring system, for output, data indicating the location within the property where the person is likely located by providing, for output, the map of the property with the location where the person is likely located.

In some implementations, the method further includes determining, by the monitoring system, that the person is likely injured based on second sensor data; and providing, for output by the monitoring system, data indicating that the person is likely injured.

In some implementations, the method further includes based on determining that the person is likely injured, generating, by the autonomous drone of the monitoring system, using an additional onboard sensor, third sensor data; based on the third sensor data, determining, by the monitoring system, a severity of the injury to the person; and providing, for output by the monitoring system, the data indicating that the person is likely injured by providing, for output, the data indicating that the person is likely injured and data indicating the severity of the injury to the person.

In some implementations, the method further includes the onboard sensor is a camera and the second sensor data is image data, and the additional onboard sensor is an ultrasound sensor and the third sensor data is ultrasound data.

In some implementations, the method further includes providing, by the monitoring system, second sensor data as an input to a model trained to identify locations of people; and determining, by the monitoring system, the location within the property where a person is likely located based on an output of the model trained to identify locations of people based on the second sensor data.

In some implementations, the method further includes receiving, by the monitoring system, labeled training data that includes first labeled sensor data that corresponds locations with people and second labeled sensor data that corresponds to locations without people; and training, by the monitoring system, using machine learning, the first labeled sensor data, and the second labeled sensor data, the model to identify locations of people based on the second sensor data.

In some implementations, the method further includes based on the second sensor data, determining, by the monitoring system, that the person is likely alive; and providing, by the monitoring system, for output, data indicating that the person is likely alive.

In some implementations, the method further includes the second sensor is a microphone and the second sensor data is audio data, and the method includes providing, by the monitoring system, the audio data as an input to a model trained to identify human sounds; and determining, by the monitoring system, that the person is likely alive based on an output of the model trained to identify human sounds.

In some implementations, the method further includes based on determining a location within the property where a person is likely located, activating, by the monitoring system, a communication channel between a device outside the property and the autonomous drone.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 4 is a flowchart of an example process for providing data corresponding to a detected individual for ultrasound analytics.

FIG. 5 is a flowchart of an example system for processing data corresponding to a detected individual for ultrasound analytics.

DETAILED DESCRIPTION

Figure 1:
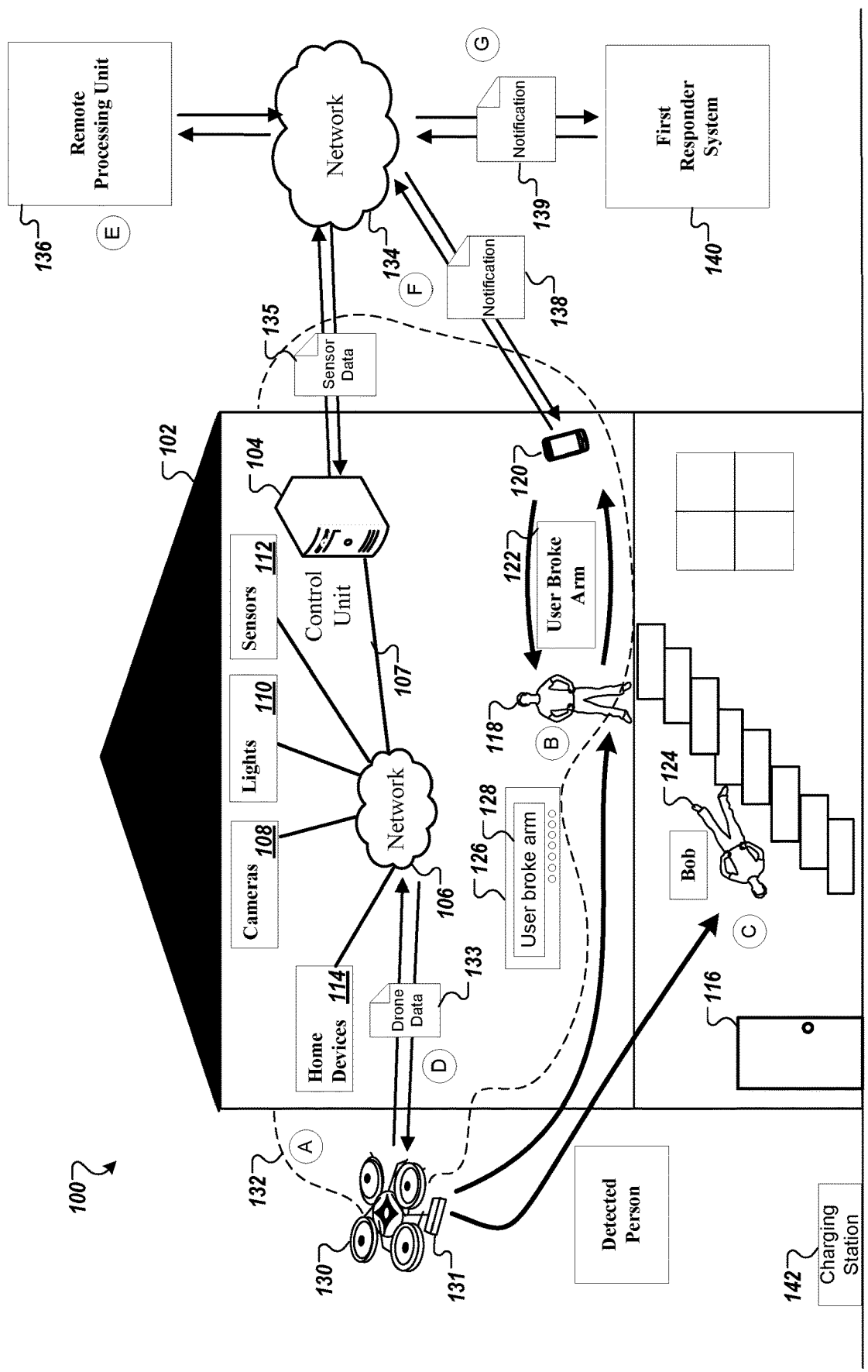
FIG. 1 is a contextual diagram of an example system of an integrated security environment for detecting one or more injured individuals at a monitored facility.

FIG. 1 is a contextual diagram of an example system 100 of an integrated security environment for detecting one or more injured individuals at a monitored facility. Though system 100 is shown and described including a particular set of components in a monitored property 102 includes a control unit server 104, network 106, cameras 108, lights 110, sensors 112, home devices 114, security panel 126, drone 130, network 134, remote processing unit 136, and first responder system 140, the present disclosure need not be so limited. For instance, in some implementations, only a subset of the aforementioned components may be used by the integrated security environment for monitoring the control unit servers in each monitored property. As an example, there may be a system 100 that does not use the lights 110. Similarly, there may be implementations that the control unit, such as control unit server 104, is stored in the remote processing unit 136. Yet other alternative systems also fall within the scope of the present disclosure such as a system 100 that does not use a control unit server 104. Rather, these systems would communicate directly with the remote processing unit 136 to perform the monitoring. For these reasons, the system 100 should not be viewed as limiting the present disclosure to any particular set of necessary components.

As shown in FIG. 1, a residential facility 102 (e.g., home) of user 118 is monitored by a control unit server 104 that includes components within the residential facility 102. The components within the residential facility 102 may include one or more cameras 108, one or more lights 110, one or more sensors 112, one or more home devices 114, and the security panel 126. The one or more cameras 110 may include video cameras that are located at the exterior of the residential facility 102 near the front door 116, as well as located at the interior of the residential facility 102 near the front door 116. The one or more sensors 112 may include a motion sensor located at the exterior of the residential facility 102, a front door sensor that is a contact sensor positioned at the front door 116, and a lock sensor that is positioned at the front door 116 and each window. The contact sensor may sense whether the front door 118, the garage door, or the window is in an open position or a closed position. The lock sensor may sense whether the front door 116 and each window is in an unlocked position or a locked position. The one or more home devices 114 may include home appliances such as a washing machine, a dryer, a dishwasher, an oven, a stove, a microwave, and a laptop, to name a few examples. The security panel 126 may receive one or more messages from a corresponding control unit server 104 and a remote processing unit 136.

The control unit server 104 communicates over a short-range wired or wireless connection over network 106 with connected devices such as each of the one or more cameras 108, one or more lights 110, one or more home devices 114 (washing machine, a dryer, a dishwasher, an oven, a stove, a microwave, a laptop, etc.), one or more sensors 112, the drone 130, and the security panel 126 to receive sensor data descriptive of events detected by the one or more cameras 108, the one or more lights 110, the done 130, and the one or more home devices 114 in the residential facility 102. In some implementations, each of the connected devices may connect via Wi-Fi, Bluetooth, or any other protocol used to communicate over network 106 to the control unit server 104. Additionally, the control unit server 104 communicates over a long-range wired or wireless connection with a remote processing unit 136 over network 134 via one or more communication links. In some implementations, the remote processing unit 136 is located remote from the residential facility 102, and manages the monitoring at the residential facility 102, as well as other (and, perhaps, many more) monitoring systems located at different properties that are owned by different users. In other implementations, the remote processing unit 136 communicates bi-directionally with the control unit server 104. Specifically, the remote processing unit 136 receives sensor data descriptive of events detected by the sensors included in the monitoring system of the residential facility 102. Additionally, the remote processing unit 136 transmits instructions to the control unit server 104 for particular events.

In some implementations, a user 118 may install a device to monitor the remote property 102 from the outside. For instance, the user 118 may install a drone 130 and a corresponding charging station 142 to monitor the activity occurring outside and inside the residential property 102. In some implementations, the control unit server 104 may detect when the drone 130 has departed from the charging station 142. The drone 130 may automatically depart from the charging station 142 at predetermined times set by the user 118 according to a signature profile. Once departed from the charging station 142, the drone 130 may fly a predetermined path 132 as set by the user according to a profile. The predetermined path 132 may be any path around the residential property 102 as described by the signature profile. The signature profile will be further explained below.

In some implementations, the drone 130 will have a set of devices 131 for providing sensor data to the control unit 104. The set of devices 131 may include a camera or an array of cameras, a GPS device, and an ultrasound transducer, to name a few examples. The drone 130 may instruct the set of devices 131 to record and monitor while the drone 130 flies the predetermined path 132.

In the example shown in FIG. 1, user 118 may be in the residential facility 102 and can arm the residential facility 102 at any point in time. In doing so, the user 118 may turn off each of the one or more lights 110, turn off each of the one or more home devices 114, lock the front door 116, and close and lock each of the one or more windows. The user 118 may interact with a client device 120 to activate a signature profile, such as "arming home" for the residential facility 102. Alternatively, the user 118 may keep the one or more lights 110 on, keep the one or more home devices 114 on while setting the "arming home" profile.

In some implementations, the client device 120 may display a web interface, an application, or a device specific application for a smart home system. The client device 120 can be, for example, a desktop computer, a laptop computer, a tablet computer, a wearable computer, a cellular phone, a smart phone, a music player, an e-book reader, a navigation system, a security panel, or any other appropriate computing device. In some implementations, the client device 120 may communicate with the control unit server 104 over the network 106. The network 106 may be wired or wireless or a combination of both and can include the Internet.

In some implementations, user 118 may communicate with the client device 120 to activate a signature profile for the residential facility 102. To illustrate, user 118 may first instruct the control unit server 104 to set a signature profile associated with arming the residential facility 102. For example, user 118 may use a voice command to say "Smart Home, arm house," to the client device 120. The voice command may include a phrase, such as "Smart Home" to trigger the client device 120 to actively listen to a command following the phrase. Additionally, the phrase "Smart Home" may be a predefined user configured term to communicate with the client device 120. The client device 120 can send the voice command to the control unit server 104 over the network 106.

In some implementations, the control unit server 104 may notify the remote processing unit 136 that the residential facility 102 is to be armed. In addition, the control unit 104 may set associated parameters in response to receiving the voice command. Moreover, the control unit 104 can send back a confirmation to the client device 120 in response to arming the residential facility 102 and setting the associated parameters. For example, the control unit server 104 may transmit a response to the client device 120 that reads "Smart Home armed."

In some implementations, in order for the control unit server 104 to allow user 118 and others to set and activate a signature profile case for the residential facility 102, the user 118 and others may define and store signature profiles in the control unit server 104. In other implementations, the user 118 and others may define and store signature profiles in the remote processing unit 136. The signature profile may be associated with each user and allow for various use cases of the devices in the residential facility 102. Each of the signature profiles can be associated with one user, such as user 118 or user 124. For example, a user 118 may create a signature profile for arming the residential facility 102. In another example, a user 122 may create a signature profile for monitoring the residential facility 102 with a drone 130 for monitoring the residential facility 102.

In some implementations, user 122 may store one or more parameters associated with a use case in his or her signature profile. Specifically, the one or more parameters for each use case may describe a volume level in decibels (dB) of the speakers 108, an aperture amount for the cameras 110, a brightness intensity level of the lights 112, turning on home devices 117 such as television, laptop, one or more fans, setting a specific temperature of a thermometer, opening or closing the shades of a window a particular amount, alarm settings corresponding to the security panel 126, defining a predetermined path and a length of time for the drone 130 to monitor the residential facility 102, and any other parameters to describe the use case. For example, user 122 may create a signature profile with a use case for "arm home". The user 122 may define a volume level of 0 dB for the speakers 108, an aperture of f/16 for the one or more cameras 110, zero lumens for the one or more lights 112, turning off a television, turning off a laptop, turning on fans, setting the thermometer to 67 degrees Fahrenheit, fully closing the blinds of the one or more windows, and setting the security panel 126 to notify the remote processing unit 136 for any detected alarms.

In some implementations, the user 118 may define a predetermined path 132 for the drone 130 to monitor around the residential facility 102. The predetermined path 132 may be drawn by the user 118 through interaction with the smart home application on the client device 120. The user 118 may additionally define the height and speed in which the drone 130 flies around the residential property 102. For instance, the user 118 may draw a circle on a map provided by the smart home application on the client device 120, set the altitude to 10 feet, and set the drone 130's flying speed to 15 miles per hour. The user 118 can define a period of time for the drone to monitor the residential property 102. For example, the user 118 may enter the time of 1 hour into the smart home application on the client device 120. Following the time period in which the drone 130 monitors the residential property 102, the user 118 can instruct the drone to return to the charging station 142 or to traverse a new predetermined path around residential property 102, different from predetermined path 132.

In some implementations, the control unit server 104 sets the parameters for the signature profile when the user 122 speaks "Smart home, arming the home" to client device 120.

The control unit server 104 saves the parameters in memory defined by the user 118 in the smart home application on the client device 120 in response to the user setting the parameters. In addition, the control unit server 104 may transmit the set parameters for the signature profile to the remote processing unit 136 to save for backup purposes.

In some implementations, the control unit server 104 may increase the sensitivity corresponding to each of the one or more sensors 114 for the "arming the home" use case. Specifically, control unit server 104 may increase the sensitivity for the front door sensor, the garage door sensor, and the lock sensor by a predetermined factor so that smaller movements of the front door or garage door trigger an alarm event. For example, the sensitivity may be increased by a factor of five.

In some implementations, the control unit server 104 may send a response to display a message on the client device 120 that says "Smart Home, home armed" once the control unit server 104 sets the parameters. The control unit server 104 may also transmit the same response to the display 128 of security panel 126 once the control unit server 104 sets the parameters. In addition, the control unit server 104 may transmit a message to the remote processing unit 126 that the residential facility 102 finished arming.

In some implementations, the drone 130's set of devices 131 may seek to detect the health of one or more individuals inside the residential facility 101. In particular, the set of devices 131 may gather information on the health of the one or more individuals inside the residential facility 102. As the drone 130 flies around the residential facility 102, the drone 130 scans areas external and internal to the residential facility 102. In particular, the drone 130 may scan areas in proximity to the residential facility 102, scan through the walls of the residential facility 102 to see the interior of the residential facility 102, and monitor each level of the residential facility 102. The drone 130 uses local machine learning algorithms along with ultrasound data, images, and GPS locational data captured by the set of devices 131 to detect one or more individuals in the residential facility 102. Should the drone 130 detect an individual in the residential facility 102, the drone 130 may move closer to the individual to perform a more detailed scan. The drone 130 then sends the captured data to the control unit server 104 for further processing to determine the health of the one or more individuals. The control unit server 104 may also acquire sensor data from the cameras 108, the lights 110, the sensors 112, and the home devices 114 in response to receiving the captured data from the drone 130. The control unit server 104 provides the captured data and the sensor data to the remote processing unit 136 for further processing a determination of whether a first responder system 140 should be contacted.

For example, during stage (A), the user 118 sets the parameters for the "arming home" signature profile that includes a time for the drone to initiate monitoring the residential property 102. At the set time as designated by the "arming home" signature profile, the control unit server 104 sends an indication to the drone 130 via network 106 to initiate monitoring the residential facility 102. The indication may include GPS coordinates of the predetermined path, the length of time to travel, and the altitude or varying altitude around the residential facility 102 in which to travel. In some implementations, the remote processing unit 136 may send an indication to the control unit server 104 to instruct the drone 130 to initiate the monitoring of the residential facility 102. In response to receiving the indication, the drone 130 powers on, flies away from the charging station 142, and flies the predetermined path 132 as set in the "arming home" signature profile. During flight, the drone 130 uses the set of sensors 131 to detect one or more individuals in the residential facility 102.

In some implementations, the control unit server 104 may use the cameras 108, the lights 110, the sensors 112, and the home devices 114 in conjunction with the set of sensors 131 to detect one or more individuals in the residential facility 102. For instance, as the drone 130 travels around the predetermined path 132, the drone 130 may send GPS coordinate updates to the control unit server 104. The control unit server 104 may turn on one or more of the lights 110 in one or more areas currently being viewed by the drone 130 to improve detectability. In addition, the control unit server 104 may increase sensitivity of one or more sensors 112 in the one or more areas currently being viewed by the drone 130 to also improve detectability. Should a motion detector from the one or more sensors 112 detect movement in an area of the residential facility 102, the control unit server 104 can transmit a GPS coordinate of the detected motion sensor to the drone 130 to focus the set of devices 131 on the area designated by the transmitted GPS coordinate. The GPS coordinate may be inside or outside the residential facility 102.

During stage (B), the drone 130 detects an individual in the residential facility 102. For instance, the set of devices 131 captures data during the drone 130's flight around the predetermined path 132. The data includes camera images and GPS locational data. The drone 130 feeds the camera images and the GPS locational data to a local processing engine included in the drone 130's memory. The local processing engine produces an indication that an individual has been detected in the camera images. In response to determining that an individual, such as user 118, has been detected, the drone 130 moves closer to that individual to perform an ultrasound scan. The drone 130 may move closer to a window of the residential facility 102 or closer to a wall of the residential facility 102 to perform the ultrasound scan. The drone 130 may perform an ultrasound scan of the user 118 at different portions of the user 118's body. For instance, the drone 130 may initiate scanning user 118's head, then move to scan the user 118's shoulder, and down to user 118's feet. These ultrasound scans will be used later in constructing a mapped environment of the user 118.

During stage (C), the drone 130 detects another individual, such as user 124, in the residential facility 102. The drone 130 performs similar steps as described in stage (B) to detect user 124. In some implementations, the local processing engine in the drone 130 produces an indication of a detected person. In other implementations, the local processing engine in the drone 130 may produce a recognition of a detected person. For instance, based on the training of the local processing engine, the local processing engine may produce an indication that a person has been detected or that the person detected is user 124 or Bob. This indication will be further described below.

During stage (D), the drone 130 provides the captured drone data 133 to the control unit server 104 over the network 106. The captured drone data 133 includes the captured images, the GPS locational data, and the indication provided by the local processing engine. The control unit server 104 receives the captured drone data 133. The control unit server 104 combines the captured drone data 133 with data provided by the one or more cameras 108, the one or more lights 110, and the one or more sensors 112. For instance, the control unit server 104 may package together the captured drone data 133 with images and video from the cameras 108, a brightness level from the one or more lights 110, and motion or contact data from the one or more sensors 112 when a detection was made by the drone 130. In addition, the control unit server 104 may include the data changes indicating the brightness level of the one or more lights 110 and the sensitivity changes of the one or more sensors 112 to improve detectability for the drone 130. This change data may facilitate the remote processing unit 136 in determining typical paths of one or more individuals in the residential facility 102. This can be used to update the predetermined path 132 of the drone 130 for improved tracking of individuals. Once the control unit server 104 packages the data, the control unit server 104 transmits the packaged data as sensor data 135 to the remote processing unit 136.

During stage (E), the remote processing unit 136 receives the sensor data 135. The remote processing unit 136 includes a remote processing engine to produce an indication of the health of the individual detected in the captured image. For instance, the remote processing engine of the remote processing unit 136 includes one or more machine learning algorithms that can produce an indication of an injury of the individual from the sensor data 135. The injuries may include one or more broken bones, external bleeding, and burn marks, to name a few examples. The indication output by the remote processing unit 136 may include an image from the ultrasound data including the detected individual and a tagged description of the injury. The remote processing engine provides the image and the tagged description of the injury to a severity indicator. The severity indicator tags the input with a number indicating the severity of the individual's health in the attached image. For example, as illustrated in FIG. 1, the control unit server 104 may provide sensor data 135 of two detected individuals in residential facility 102, user 118 and user 124. The remote processing engine of the remote processing unit 136 may produce a severity indication of zero, corresponding to one or more images from the ultrasound data of user 118. The severity indication of zero indicates that user 118 has no injury or appears to have no injury. Likewise, the remote processing engine may produce a severity indication of ten, corresponding to one or more images from the ultrasound data of user 124, indicating a severe injury. The remote processing engine may detect that user 124 has broken his arm, as illustrated by the images in the ultrasound data.

During stage (F), the remote processing engine provides a notification to the owner of the residential facility 102. The notification includes one or more images and the corresponding severity of an injury of an identified individual in each of the one or more images. In some implementations, the remote processing engine in the remote processing unit 136 provides the notification to the client device 120 of user 118. The client device 120 may display the one or more images and the corresponding severity of the injury of the identified individual in each of the one or more images to the user 118. For example, the severity of the injury may include a number such as ten or display a message that recites "User Broke Arm" 122, as illustrated in FIG. 1. The user 118 may proceed to locate the injured individual, user 124, to provide emergency assistance.

During stage (G), the remote processing engine provides a notification to a first responder system 140. The notification includes a reconstructed mapped environment of the images of the ultrasound scans and a corresponding severity indicator for each of the images. As mentioned above, the reconstructed mapped environment may include an image converted from ultrasound of user 118's head, user 118's shoulders, user 118's chest, and the remaining body sections down to user 118's feet. Each of these ultrasound images reconstructed in the mapped environment may include a severity indicator. For instance, for user 124 that broke his arm, the severity indicator corresponding to the head of user 124 may be zero, the severity indicator corresponding to the shoulder of user 124 may be one, the severity indicator corresponding to the arms of user 124 may be ten, and the severity indicator corresponding to the legs of user 124 may be two. This reconstructed mapped environment is provided to the first responder system 140 to facilitate determining an injury of the user, such as user 124. In some implementations, the first responder system 140 may be police officers, firefighters, paramedics, and emergency medical technicians, to name a few examples.

Figure 2:
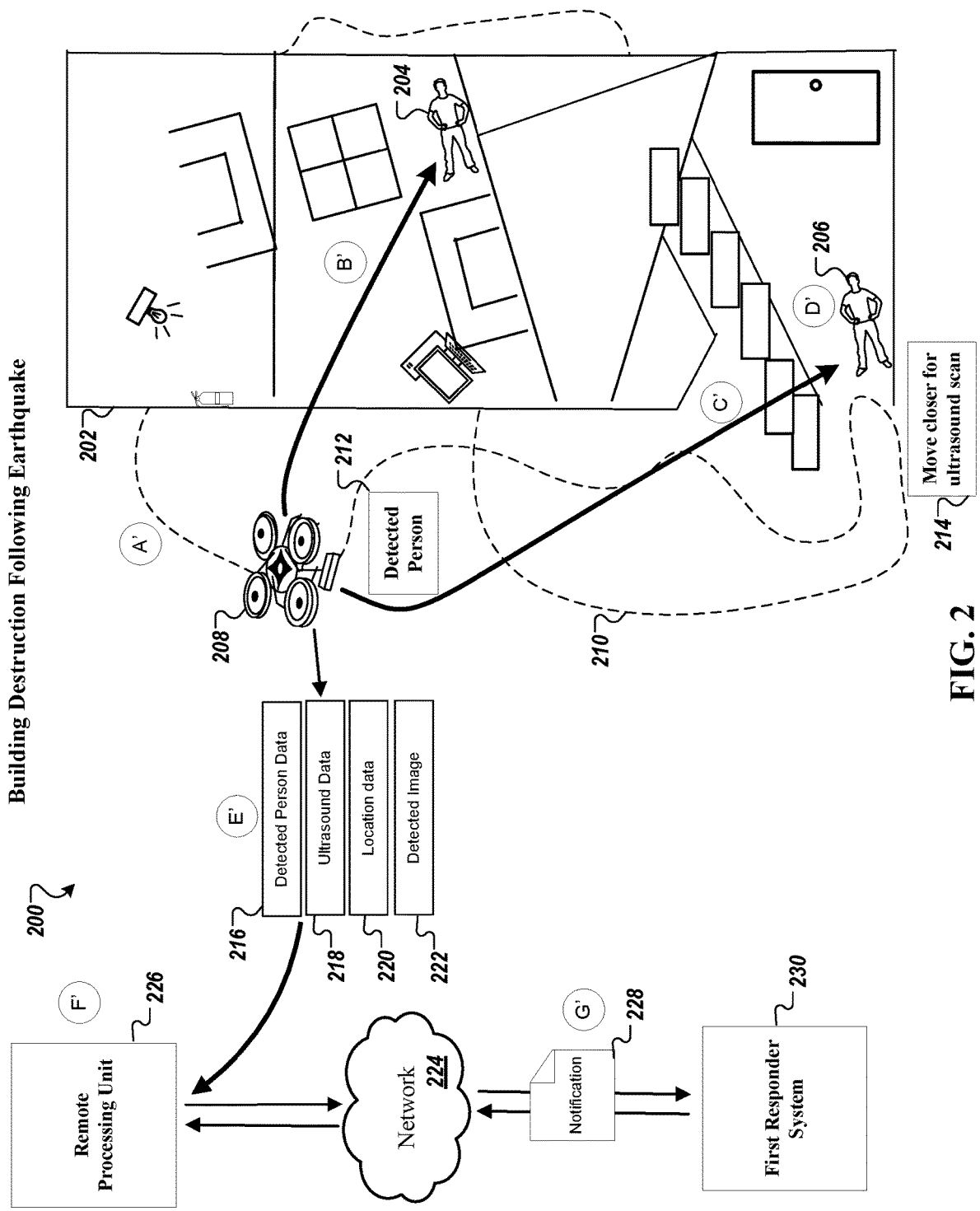
FIG. 2 is a contextual diagram of an example system of a building destruction environment for detecting one or more injured individuals.

FIG. 2 is a contextual diagram of an example system of a building destruction environment 200 for detecting one or more injured individuals. The building destruction environment 200 includes a demolished building 202 as a result of a natural disaster, such as an earthquake. The demolished building 202 includes one or more trapped individuals that may have life threatening injuries. For instance, the demolished building 202 includes user 204 lying down on the second floor of the demolished building 202 and user 206 lying under the rubble at the bottom of the demolished building 202. In some implementations, a first responder, such as a firefighter or a police officer, may let drone 208 fly around a path 210 around the demolished building 202 to find the one or more trapped individuals to detect their health status.

FIG. 2 is similar to FIG. 1 without the inclusion of a control unit server 104 and one or more sensors at the demolished building 202. The only data provided to the remote processing unit 226 includes data retrieved from the drone 208 itself. In addition, the drone 208 can scan along path 210 until retrieved by a first responder via a client device.

During stage (A'), which is similar to stage (A) of FIG. 1, the drone 208 flies a path 210 to find one or more individuals trapped in the demolished building 202. In some implementations, the path 210 may be preprogrammed by the first responder located at the scene of the building destruction environment 200. In other implementations, the path 210 may be a random path taken by the drone 208 around the demolished building 202. The drone 208 may fly the path 210 until a first responder retrieves the drone 208. In some implementations, the drone 208 may fly the path 210 until the first responder or first responder system 230 receives an indication from the remote processing unit 226 indicating a location of the one or more individuals in the demolished building 202 and a corresponding health status of the located one or more individuals.

During stages (B') and (C'), which are similar to stages (B) and (C) of FIG. 1, the drone 208 detects user 204 and user 206 in the demolished building 202, as illustrated by the arrows of detected person 212. Initially, the drone 208 utilizes the camera and GPS device from the set of sensors onboard the drone 208 to detect user 204 and 206 in the demolished building 202. The drone 208 utilizes a local processing engine that uses one or more machine learning algorithms to detect individuals from the captured images. Once the local processing engine identifies one or more individuals in the captured images, the local processing engine tags the individuals in the image with GPS locational data from the GPS device. The GPS locational data describes the locational position of the detected individual. For instance, the drone 208 calculates the locational position of the detected individual using the GPS locational position of the drone 208, the altitude of the drone 208, and an estimated distance between the drone 208 and the detected individual using slope estimation.

During stage (D'), the drone 208 moves closer to a detected individual to perform an ultrasound scan. In order to ensure a high quality ultrasound results, the drone 208 may be programmed to move as close as possible to the detected individual, such as user 206 collapsed under the rubble. The drone 208 may perform a full body ultrasound scan to capture all features of user 206. In some implementations, one or more portions of user 206's body may be covered by rubble. The drone 208 may only perform scans on the exposed portion of user 206's body. Following the ultrasound scans of the user 206's body, the drone 208 may move to the next detected individual, such as user 204, to perform the ultrasound scan on user 204. In some implementations, the drone 208 may receive an audible sound coming from the user 204 while performing the ultrasound scan. If the drone 208 determines the audible sound is greater than a threshold level, such as the user 204 is screaming or moaning in pain, the drone 208 can include an emergency request of the user 204 in danger in the data to provide to the remote processing unit 226. In addition, the drone 208 can initiate communication with a first responder system 230 if the drone 208 determines the user 204 is in severe danger based on the audible sound being greater than the threshold level. Alternatively, the drone 208 can provide an indication to the user 204 to keep calm. For instance, the drone 208 can play a calming song or the drone 208 can play an audible message to the user 204 that recites "Please remain calm, help is on the way." The drone 208 may recite other messages to the user 204. Alternatively, the drone 208 may cease performing ultrasound scan if the drone 208 determines the user 204 is scared. Afterwards, the drone 208 may return to the path 210 to find any other individuals in the demolished building 202.

During stage (E'), the drone 208 transmits data to the remote processing unit 226. The data includes detected person data 216, ultrasound data 218, location data 220, and detected image data 222. The detected person data 216 includes information corresponding to the number of individuals detected during the drone 208's scan on path 210. For example, the detected person data 216 may indicate that two individuals, user 204 and user 206, were detected in the demolished building 202. The ultrasound data 218 may include the ultrasound scans of the exposed body portions of user 204 and user 206. The location data 220 may include the GPS locational data of user 204 and user 206. The detected image data 222 may include the images from the drone 208's camera that include the detected individuals and non-detected images. In some implementations, the images may include a tag indicating whether an individual is detected or not detected in that image.

During stage (F'), which is similar to stage (E) of FIG. 1, the remote processing engine in the remote processing unit 226 processes the detected person data 216, the ultrasound data 218, the location data 220, and the detected image data 222 to produce an indication of the health of the one or more detected individuals.

During stage (G'), which is similar to stage (G) of FIG. 1, the remote processing engine provides a notification 228 to the first responder system 230. As mentioned earlier, the notification includes a reconstructed mapped environment of the images of the ultrasound scans and a corresponding severity indicator for each of the images.

In another exemplary use case, a drone, such as drone 208, can fly a particular path around a vehicular accident to locate one or more individuals trapped in the vehicles. The drone 208 may or may not be programmed with a predetermined path 210 by a first responder. In particular, the drone 208 can be programmed to monitor an area that includes the vehicular accident. For example, the drone 208 can fly above the vehicular accident, near the windows of the vehicles involved in the accident, and low to the ground to search underneath the vehicles to determine whether an individual has been trapped underneath the vehicle. The drone 208 can perform steps similar to that of FIG. 1 and FIG. 2 to notify first responders if one or more injured individuals are found.

In another exemplary use case, drone 208 can fly a particular path around a search and rescue area in a forest to locate one or more lost individuals. The drone 208 may or may not be programmed with a predetermined path 210 by a first responder to fly through the forest searching for the lost individuals. If the drone 208 detects a lost individual, the drone 208 can perform steps similar to that of FIG. 1 and FIG. 2 to notify first responders and determine if the detected individual is injured.

Figure 3:
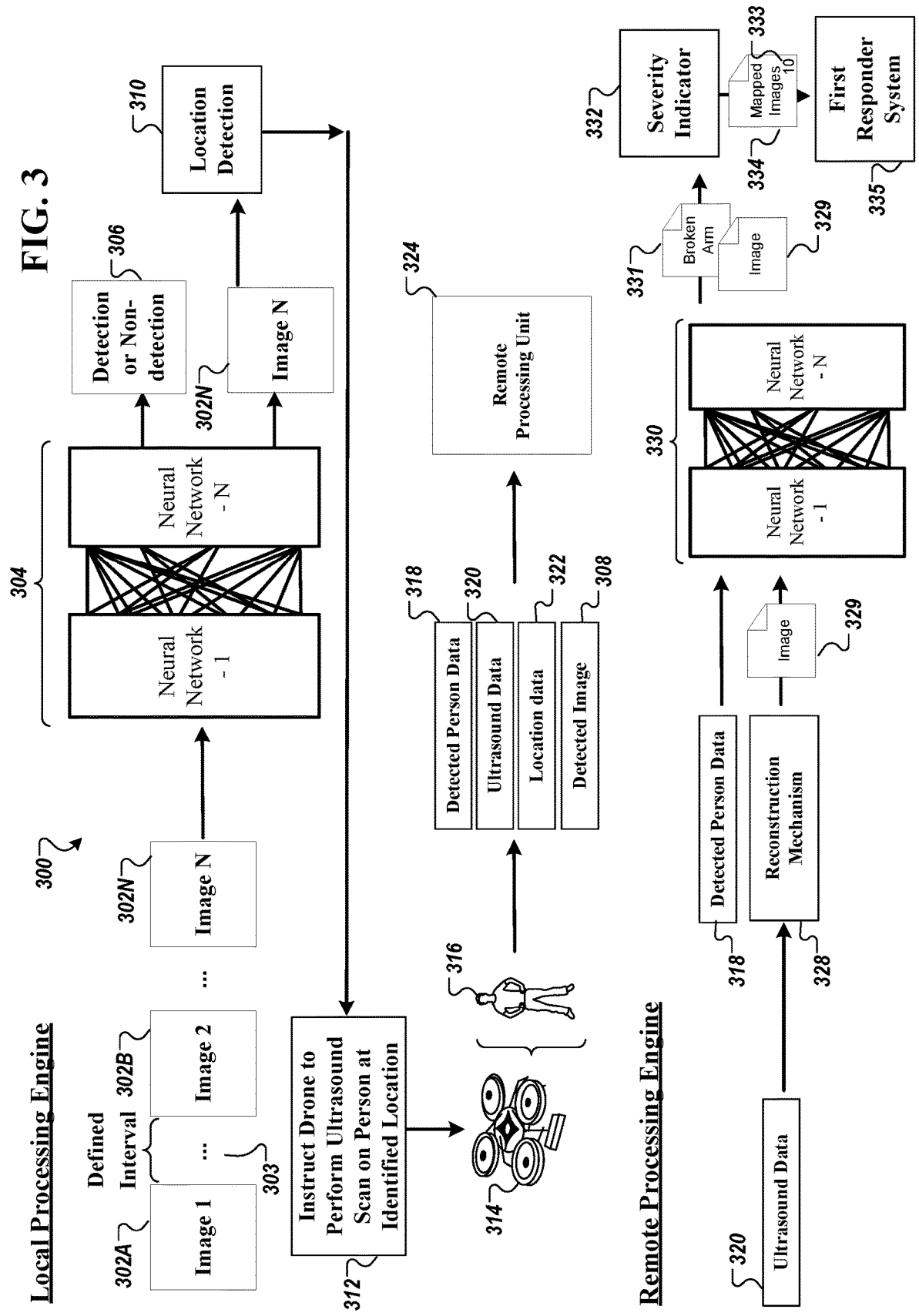
FIG. 3 is a contextual diagram of an example system for training a neural network model for ultrasound analytics.

FIG. 3 is a contextual diagram of an example system 300 for training a neural network model for ultrasound analytics. The system 300 can train other types of machine learning models for ultrasound analytics, such as one or clustering models, one or more deep learning models, Bayesian learning models, or any other type of model. Briefly, and as described in more detail below, the system 300 illustrates the application of a neural network model in the local processing engine of the drone 130 and the application of a neural network model in the remote processing engine of the remote processing unit 136. In some implementations, the data provided as input to the model in the local processing engine comes from the set of sensors 131 mounted on the drone 314. In some implementations, the data provided as input to the model in the remote processing engine comes from an output of analyzing the sensor data processed by the local processing engine.

In some implementations, the local processing engine in the drone 314 trains a neural network model while the drone 314 is offline. The neural network model may include an input layer, an output layer, and one or more hidden layers. The local processing engine may use a machine learning technique to continuously train the neural network model. The local processing engine trains its neural network model using one or more training techniques. For instance, the local processing engine may train the neural network model using images that include zero or more individuals and a tag as to whether or not an individual exists in the image. The local processing engine applies the neural network model once sufficiently trained.

In some implementations, the local processing engine in the drone 314 applies images captured from the camera mounted on the drone 130 to the trained model 304. The drone 314 sequentially inputs each image 302A-302N to the trained model 304 at a predetermined time interval. For instance, the predetermined time interval may be the length of time it takes for the trained model 304 to process one image 302C. In another instance, the predetermined time interval may be spaced by a time, such as 2 seconds.

In some implementations, the trained model 304 produces an output for each image input to the trained model 304. The output of the trained model 304 includes a detection or non-detection 306 and the input image 302N. The detection or non-detection 306 includes an indication of whether a person is detected in the image 302N. If a person is not detected in an image, such as image 302N, the local processing engine tags the image as no individual detected. Alternatively, if the local processing engine indicates a detection in 306, the image 302N is provided as input to the location detection 310. In the location detection 310, the local processing engine calculates the locational position of the detected individual using the GPS location position of the drone 314, the altitude of the drone 314, and an estimated distance between the drone 314 and the detected individual using slope estimation. The image 302N is tagged with the locational position of the detected individual.

In some implementations, the local processing engine instructs the drone 314 to perform an ultrasound scan at the locational position of the detected individual, such as user 316, based on the determination that the image 302N includes user 316. The drone 314 moves in proximity to the location of the user 316 and performs ultrasound scans of the user 316 over different portions of the user 316's body. For instance, the drone 314 may initiate scanning user 316's head, then move to scan the user 316's shoulders, and down to user 316's feet to capture all features of user 316. This ensures all parts of user 316 can be checked for a health status.

After performing the ultrasound scans, the drone 314 provides the captured data to a remote processing unit 324. As mentioned earlier in FIG. 2, the drone 314 provides the detected person data 318, the ultrasound data 320, the location data 322, and the detected image data 308 to the remote processing unit 324. In some implementations, the drone 314 provides a new set of detected person data 318, ultrasound data 320, location data 322, and detected image data 308 each time a new ultrasound scan is performed on a newly detected individual. In other implementations, the drone 314 provides a new set of data each time the drone 314 comes in contact with the charging station 142. As transmission of data to the control unit server 104 or the remote processing unit 324 draws battery usage that may be used for other purposes, such as flying or providing power to the set of device 131 mounted on-board the drone 314, the drone 314 may be configured to only transmit data when connected to the charging station 142 to preserve battery life when monitoring the residential facility 102.

In some implementations, the remote processing unit 324 receives the detected person data 318, the ultrasound data 320, the location data 322, and the detected image data 308. The remote processing engine in the remote processing unit 324 processes each of the received data pieces. Initially, the remote processing engine provides the ultrasound data 320 to a reconstruction mechanism 328. First, the reconstruction mechanism 328 converts each scan of ultrasound into an image 329. For example, if the drone 314 performs ten ultrasound scans on user 316, then the reconstruction mechanism 316 converts the ten ultrasound scans to ten corresponding images.

In some implementations, the remote processing engine provides each image 329 converted from an ultrasound scan to a trained neural network model 330. The trained model 330 is similar to trained model 304. In particular, the trained model 330 may include an input layer, an output layer, and one or more hidden layers. The remote processing engine may use a machine learning technique to continuously train the neural network model to create the trained model 330. The remote processing engine applies the trained model 330 once sufficiently trained.

In some implementations, the remote processing engine in the remote processing unit 324 applies images 329 of the ultrasound data and the detected person data 318 to the trained model 330. The trained model 330 is trained to produce an indication 331 of the health of the individual detected in the image from the captured ultrasound. For example, the health of the individual 316 may include indicating whether the individual has sustained one or more broken bones, any external bleeding, or burn marks, to name a few examples. The remote processing engine may tag the input image 329 with the indication 331.

In some implementations, the remote processing engine may provide the tagged input image 329 with the indication 331 output from the trained model 330 to a severity indicator mechanism 332. The severity indicator mechanism 332 analyzes the tagged description 331 to determine a severity indicator 333 of the individual in the image 329. For instance, the severity indicator 333 indicates a number that indicates the severity of the individual's health according to the tagged description. For instance, if the tagged description indicated "external bleeding," the severity indicator mechanism 332 may provide a severity indication of ten. In another instance, if the tagged description indicated "broken arm," the severity indicator mechanism 332 may provide a severity indication of seven. This is because an external bleeding symptom may be more severe than a broken arm, depending on the severity of the external bleeding.

In some implementations, the severity indicator mechanism 332 reconstructs a mapped environment 334 using the images converted from the ultrasound scans and the corresponding severity indicator for each of the images. For example, the severity indicator mechanism 332 reconstructs the mapped environment of the images of the ultrasound scan performed on user 316. The reconstructed mapped environment 334 may include an image converted from ultrasound of user 316's head, user 316's shoulders, user 316's chest, and the remaining body sections down to user 316's feet. Each of these images reconstructed in the mapped environment may include a severity indicator 333. For instance, for user 316 who may have a broken leg, the severity indicator mechanism 332 may designate a severity indicator of zero to the head of user 316, a severity indicator of one corresponding to the shoulder of user 316, a severity indicator of zero corresponding to the arms of user 316, and a severity indicator of ten corresponding to the legs of user 316. The remote processing engine provides the reconstructed map 334 to the first responder system 335 to facilitate in determining an injury of an identified user.

In some implementations, the first responder system 335 can further train the trained model 330. For instance, after the first responder system 335 receives the reconstructed map 334, an individual, such as a medic, of the first responder system 335 may determine that the user 316 does not in fact have a broken leg, as determined by the trained model 330. In response, the medic of the first responder system 335 can update one or more medical reports that the trained model 330 accesses to generate a reconstructed mapped environment 334 to reflect a change to the medical diagnosis of the leg of user 316.

In some implementations, the first responder system 335 may store the medical reports and transfer the medical records to the remote processing unit 226. The remote processing engine may access the medical records for retraining the trained model 330. For instance, rather than the medical diagnosis indicating the leg of user 316 as being broken, the medical diagnosis in the medial reports indicates that the user 316's leg is healthy. The trained model 330 can access the received updated reports and the corresponding image 329 used in the reconstructed mapped environment 334 to retrain the trained model 330 to identify that the leg of user 316 in the image 329 is not broken. The trained model 330 can be retrained with other medical diagnosis updates for user 316 and other users.

FIG. 4 is a flowchart of an example process 400 for providing data corresponding to a detected individual for ultrasound analytics. Generally, the process 400 includes determining an indication of an individual in a frame of image data; determining a location of the identified individual in the frame of data using locational coordinates; obtaining ultrasound data of the identified individual in response to a drone's movement in proximity to the location of the identified individual to capture the ultrasound data; and, providing the identification of the individual, the location of the identified individual, the frame of image data, and the ultrasound data of the identified individual to a remote processing unit.

During 402, the drone 130 determines an identification of an individual in a frame of image data. The drone 130's set of devices 131 captures data during the drone 130's flight around the predetermined path 132. The data includes camera images and GPS locational data. The drone 130 feeds the camera images and the GPS locational data to a local processing engine included in the drone 130's memory. The local processing engine produces an indication that an individual has been detected in the camera images. In particular, the local processing engine in the drone 340 applies images captured from the camera mounted on the drone 130 to a trained neural network model 304. The trained neural network model 304 produces an output for each image that indicates a detection of a person or a non-detection of a person in the image.

During 404, the local processing engine determines a location of the identified individual in the frame of data using locational coordinates. In some implementations, the local processing engine calculates the locational position of the detected individual using the GPS location position of the drone 314, the altitude of the drone 314, and an estimated distance between the drone 314 and the detected individual using slope estimation. The image 302N is tagged with the locational position of the detected individual.

During 406, the local processing engine obtains ultrasound data of the identified individual in response to drone 130's movement in proximity to the location of the identified individual to capture the ultrasound data. In some implementations, the local processing engine instructs the drone 314 to perform an ultrasound scan at the locational position of the detected individual, such as user 316, based on the determination the image 302N detects the user 316. The drone 314 moves in proximity to the position of the user 316 and performs ultrasound scans of the user 316 over different portions of the user 316's body. For instance, the drone 314 may initiate scanning user 316's head, then move to scan the user 316's shoulders, and proceed down to user 316's feet to capture all features of user 316. This ensures all parts of user 316 can be checked for a health status.

During 408, the local processing engine provides the identification of the individual, the location of the identified individual, the frame of image data, and the ultrasound data of the identified individual to a remote processing unit. In some implementations, the drone 314 transmits the detected person data 318, the ultrasound data 320, the location data 322, and the detected image data 308 to the remote processing unit 324. In some implementations, the drone 314 provides a new set of detected person data 318, ultrasound data 320, location data 322, and detected image data 308 each time a new ultrasound scan is performed on a newly detected individual. The detected person data 318 includes information corresponding to the number of individuals detected during the drone 314's scan on path. The location data 322 may include the GPS locational data of user 316. The detected image data 308 may include the images from the drone 314's camera that include the detected individuals and non-detected images. In some implementations, the images may include a tag indicating whether an individual is detected or not detected in that image.

FIG. 5 is a flowchart of an example 500 for processing data corresponding to a detected individual for ultrasound analytics. Generally, the process 500 includes obtaining an identification of an individual, a location of the identified individual, a frame of image data, and ultrasound data of the identified individual from a drone; generate an ultrasound image from obtained ultrasound data; determine whether the ultrasound image includes the identified individual as having an injury; generate a severity indicator corresponding to each of the ultrasound images; generate a mapped environment that includes the ultrasound images stitched together that includes the corresponding severity indicator for each of the ultrasound images; and, providing the mapped environment to a first responder system.

During 502, the remote processing engine obtains an identification of an individual, a location of the identified individual, a frame of image data, and ultrasound data of the identified individual from a drone 130. In some implementations, the remote processing unit 324 receives the detected person data 318, the ultrasound data 320, the location data 322, and the detected image data 308. The remote processing engine in the remote processing unit 324 processes each of the received data items.

During 504, the remote processing engine generates an ultrasound image from the obtained ultrasound data. In some implementations, the remote processing engine provides the ultrasound data 320 to a reconstruction mechanism 328. First, the reconstruction mechanism 328 may convert each scan of ultrasound into an image 329. For example, if the drone 314 performs ten ultrasound scans on user 316, then the reconstruction mechanism 316 converts the ten ultrasound scans to ten corresponding images.

During 506, the remote processing engine determines whether the ultrasound image includes the identified individual as having an injury. In some implementations, the remote processing engine provides each image converted from an ultrasound scan to a trained neural network model 330. The trained model 330 is trained to produce an indication 331 of the health of the individual detected in the image from the captured ultrasound. For example, the health of the individual 316 may include an indication of whether the individual has sustained one or more broken bones, any external bleeding, or burn marks, to name a few examples. The remote processing engine may tag the input image 329 with the indication 331.

During 508, the remote processing engine generates a severity indicator corresponding to each of the ultrasound images. In some implementations, the remote processing engine may provide the tagged input image 329 with the indication 331 output from the trained model 330 to a severity indicator mechanism 332. The severity indicator mechanism 332 analyzes the tagged description 331 to determine a severity indicator 333 of the individual in the image 329. For instance, the severity indicator 333 indicates a number that indicates the severity of the individual's health according to the tagged description. For instance, if the tagged description indicated "external bleeding," the severity indicator mechanism 332 may provide a severity indication of ten. In another instance, if the tagged description indicated "broken arm," the severity indicator mechanism 332 may provide a severity indication of seven. This is because an external bleeding symptom may be more severe than a broken arm, depending on the severity of the external bleeding.

During 510, the remote processing engine generates a mapped environment that includes the ultrasound images stitched together that includes the corresponding severity indicator for each of the ultrasound images. In some implementations, the severity indicator mechanism 332 reconstructs a mapped environment 334 using the images converted from the ultrasound scans and the corresponding severity indicator for each of the images. For example, the severity indicator mechanism 332 reconstructs the mapped environment of the images of the ultrasound scan performed on user 316. The reconstructed mapped environment 334 may include an image converted from ultrasound of user 316's head, user 316's shoulders, user 316's chest, and the remaining body sections down to user 316's feet. Each of these images reconstructed in the mapped environment may include a severity indicator 333. For instance, for user 316 who may have a broken leg, the severity indicator mechanism 332 may designate a severity indicator of zero to the head of user 316, a severity indicator of one corresponding to the shoulder of user 316, a severity indicator of zero corresponding to the arms of user 316, and a severity indicator of ten corresponding to the legs of user 316.

During 512, the remote processing engine provides the mapped environment to a first responder system. In some implementations, providing the reconstructed mapped environment 334 to the first responder system 335 facilitates in determining an injury of an identified user.

Figure 6:
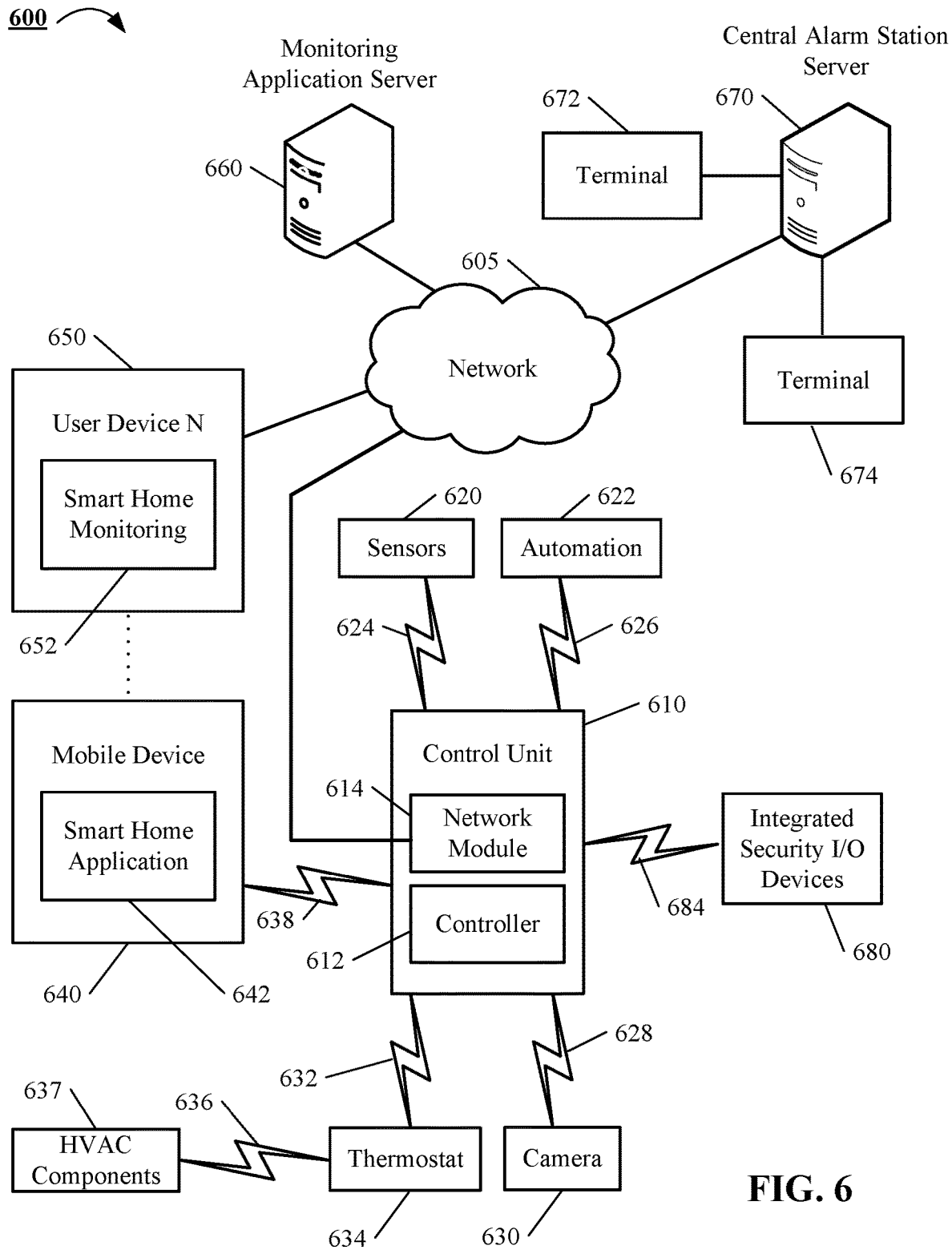
FIG. 6 is a block diagram of an example integrated security environment for ultrasound analytics that may utilize various security components.

FIG. 6 is a block diagram of an example integrated security environment 600 for ultrasound analytics that may utilize various components. The electronic system 600 includes a network 605, a control unit 610, one or more user devices 640 and 650, a monitoring application server 660, and a central alarm station server 670. In some examples, the network 605 facilitates communications between the control unit 610, the one or more user devices 640 and 650, the monitoring application server 660, and the central alarm station server 670.

The network 605 is configured to enable exchange of electronic communications between devices connected to the network 605. For example, the network 605 may be configured to enable exchange of electronic communications between the control unit 610, the one or more user devices 640 and 650, the monitoring application server 660, and the central alarm station server 670. The network 605 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 605 may include multiple networks or subnetworks, each of which may include, for example, a wired or wireless data pathway. The network 605 may include a circuit-switched network, a packet-switched data network, or any other network able to carry electronic communications (e.g., data or voice communications). For example, the network 605 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 605 may include one or more networks that include wireless data channels and wireless voice channels. The network 605 may be a wireless network, a broadband network, or a combination of networks including a wireless network and a broadband network.

The control unit 610 includes a controller 612 and a network module 614. The controller 612 is configured to control a control unit monitoring system (e.g., a control unit system) that includes the control unit 610. In some examples, the controller 612 may include a processor or other control circuitry configured to execute instructions of a program that controls operation of a control unit system. In these examples, the controller 612 may be configured to receive input from sensors, flow meters, or other devices included in the control unit system and control operations of devices included in the household (e.g., speakers, lights, doors, etc.). For example, the controller 612 may be configured to control operation of the network module 614 included in the control unit 610.

The network module 614 is a communication device configured to exchange communications over the network 605. The network module 614 may be a wireless communication module configured to exchange wireless communications over the network 605. For example, the network module 614 may be a wireless communication device configured to exchange communications over a wireless data channel and a wireless voice channel. In this example, the network module 614 may transmit alarm data over a wireless data channel and establish a two-way voice communication session over a wireless voice channel. The wireless communication device may include one or more of a LTE module, a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 614 also may be a wired communication module configured to exchange communications over the network 605 using a wired connection. For instance, the network module 614 may be a modem, a network interface card, or another type of network interface device. The network module 614 may be an Ethernet network card configured to enable the control unit 610 to communicate over a local area network and/or the Internet. The network module 614 also may be a voiceband modem configured to enable the alarm panel to communicate over the telephone lines of Plain Old Telephone Systems (POTS).

The control unit system that includes the control unit 610 includes one or more sensors. For example, the monitoring system may include multiple sensors 620. The sensors 620 may include a lock sensor, a contact sensor, a motion sensor, or any other type of sensor included in a control unit system. The sensors 620 also may include an environmental sensor, such as a temperature sensor, a water sensor, a rain sensor, a wind sensor, a light sensor, a smoke detector, a carbon monoxide detector, an air quality sensor, etc. The sensors 620 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some examples, the sensors 620 may include a radio-frequency identification (RFID) sensor that identifies a particular article that includes a pre-assigned RFID tag.

The control unit 610 communicates with the module 622 and the camera 630 to perform monitoring. The module 622 is connected to one or more devices that enable home automation control. For instance, the module 622 may be connected to one or more lighting systems and may be configured to control operation of the one or more lighting systems. Also, the module 622 may be connected to one or more electronic locks at the property and may be configured to control operation of the one or more electronic locks (e.g., control Z-Wave locks using wireless communications in the Z-Wave protocol. Further, the module 622 may be connected to one or more appliances at the property and may be configured to control operation of the one or more appliances. The module 622 may include multiple modules that are each specific to the type of device being controlled in an automated manner. The module 622 may control the one or more devices based on commands received from the control unit 610. For instance, the module 622 may cause a lighting system to illuminate an area to provide a better image of the area when captured by a camera 630.

The camera 630 may be a video/photographic camera or other type of optical sensing device configured to capture images. For instance, the camera 630 may be configured to capture images of an area within a building or within a residential facility 102 monitored by the control unit 610. The camera 630 may be configured to capture single, static images of the area and also video images of the area in which multiple images of the area are captured at a relatively high frequency (e.g., thirty images per second). The camera 630 may be controlled based on commands received from the control unit 610.

The camera 630 may be triggered by several different types of techniques. For instance, a Passive Infra-Red (PIR) motion sensor may be built into the camera 630 and used to trigger the camera 630 to capture one or more images when motion is detected. The camera 630 also may include a microwave motion sensor built into the camera and used to trigger the camera 630 to capture one or more images when motion is detected. The camera 630 may have a "normally open" or "normally closed" digital input that can trigger capture of one or more images when external sensors (e.g., the sensors 620, PIR, door/window, etc.) detect motion or other events. In some implementations, the camera 630 receives a command to capture an image when external devices detect motion or another potential alarm event. The camera 630 may receive the command from the controller 612 or directly from one of the sensors 620.

In some examples, the camera 630 triggers integrated or external illuminators (e.g., Infra-Red, Z-wave controlled "white" lights, lights controlled by the module 622, etc.) to improve image quality when the scene is dark. An integrated or separate light sensor may be used to determine if illumination is desired and may result in increased image quality.

The camera 630 may be programmed with any combination of time/day schedules, system "arming state", or other variables to determine whether images should be captured or not when triggers occur. The camera 630 may enter a low-power mode when not capturing images. In this case, the camera 630 may wake periodically to check for inbound messages from the controller 612. The camera 630 may be powered by internal, replaceable batteries if located remotely from the control unit 610. The camera 630 may employ a small solar cell to recharge the battery when light is available. Alternatively, the camera 630 may be powered by the controller's 612 power supply if the camera 630 is co-located with the controller 612.

In some implementations, the camera 630 communicates directly with the monitoring application server 660 over the Internet. In these implementations, image data captured by the camera 630 does not pass through the control unit 610 and the camera 630 receives commands related to operation from the monitoring application server 660.

The system 600 also includes thermostat 634 to perform dynamic environmental control at the property. The thermostat 634 is configured to monitor temperature and/or energy consumption of an HVAC system associated with the thermostat 634, and is further configured to provide control of environmental (e.g., temperature) settings. In some implementations, the thermostat 634 can additionally or alternatively receive data relating to activity at a property and/or environmental data at a property, e.g., at various locations indoors and outdoors at the property. The thermostat 634 can directly measure energy consumption of the HVAC system associated with the thermostat, or can estimate energy consumption of the HVAC system associated with the thermostat 634, for example, based on detected usage of one or more components of the HVAC system associated with the thermostat 634. The thermostat 634 can communicate temperature and/or energy monitoring information to or from the control unit 610 and can control the environmental (e.g., temperature) settings based on commands received from the control unit 610.

In some implementations, the thermostat 634 is a dynamically programmable thermostat and can be integrated with the control unit 610. For example, the dynamically programmable thermostat 634 can include the control unit 610, e.g., as an internal component to the dynamically programmable thermostat 634. In addition, the control unit 610 can be a gateway device that communicates with the dynamically programmable thermostat 634.

A module 637 is connected to one or more components of an HVAC system associated with a property, and is configured to control operation of the one or more components of the HVAC system. In some implementations, the module 637 is also configured to monitor energy consumption of the HVAC system components, for example, by directly measuring the energy consumption of the HVAC system components or by estimating the energy usage of the one or more HVAC system components based on detecting usage of components of the HVAC system. The module 637 can communicate energy monitoring information and the state of the HVAC system components to the thermostat 634 and can control the one or more components of the HVAC system based on commands received from the thermostat 634.

In some examples, the system 600 further includes one or more robotic devices. The robotic devices may be any type of robots that are capable of moving and taking actions that assist in security monitoring. For example, the robotic devices may include drones that are capable of moving throughout a property based on automated control technology and/or user input control provided by a user. In this example, the drones may be able to fly, roll, walk, or otherwise move about the property. The drones may include helicopter type devices (e.g., quad copters), rolling helicopter type devices (e.g., roller copter devices that can fly and also roll along the ground, walls, or ceiling) and land vehicle type devices (e.g., automated cars that drive around a property). In some cases, the robotic devices may be robotic devices that are intended for other purposes and merely associated with the system 600 for use in appropriate circumstances. For instance, a robotic vacuum cleaner device may be associated with the monitoring system 600 as one of the robotic devices and may be controlled to take action responsive to monitoring system events.

In some examples, the robotic devices automatically navigate within a property. In these examples, the robotic devices include sensors and control processors that guide movement of the robotic devices within the property. For instance, the robotic devices may navigate within the property using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about a space. The robotic devices may include control processors that process output from the various sensors and control the robotic devices to move along a path that reaches the desired destination and avoids obstacles. In this regard, the control processors detect walls or other obstacles in the property and guide movement of the robotic devices in a manner that avoids the walls and other obstacles.

In addition, the robotic devices may store data that describes attributes of the property. For instance, the robotic devices may store a floorplan and/or a three-dimensional model of the property that enables the robotic devices to navigate the property. During initial configuration, the robotic devices may receive the data describing attributes of the property, determine a frame of reference to the data (e.g., a home or reference location in the property), and navigate the property based on the frame of reference and the data describing attributes of the property. Further, initial configuration of the robotic devices also may include learning of one or more navigation patterns in which a user provides input to control the robotic devices to perform a specific navigation action (e.g., fly to an upstairs bedroom and spin around while capturing video and then return to a home charging base). In this regard, the robotic devices may learn and store the navigation patterns such that the robotic devices may automatically repeat the specific navigation actions upon a later request.

In some examples, the robotic devices may include data capture and recording devices. In these examples, the robotic devices may include one or more cameras, one or more motion sensors, one or more microphones, one or more biometric data collection tools, one or more temperature sensors, one or more humidity sensors, one or more air flow sensors, and/or any other types of sensors that may be useful in capturing monitoring data related to the property and users in the property. The one or more biometric data collection tools may be configured to collect biometric samples of a person in the home with or without contact of the person. For instance, the biometric data collection tools may include a fingerprint scanner, a hair sample collection tool, a skin cell collection tool, and/or any other tool that allows the robotic devices to take and store a biometric sample that can be used to identify the person (e.g., a biometric sample with DNA that can be used for DNA testing).

In some implementations, the robotic devices may include output devices. In these implementations, the robotic devices may include one or more displays, one or more speakers, and/or any type of output devices that allow the robotic devices to communicate information to a nearby user.

The robotic devices also may include a communication module that enables the robotic devices to communicate with the control unit 610, each other, and/or other devices. The communication module may be a wireless communication module that allows the robotic devices to communicate wirelessly. For instance, the communication module may be a Wi-Fi module that enables the robotic devices to communicate over a local wireless network at the property. The communication module further may be a 900 MHz wireless communication module that enables the robotic devices to communicate directly with the control unit 610. Other types of short-range wireless communication protocols, such as Bluetooth, Bluetooth LE, Zwave, Zigbee, etc., may be used to allow the robotic devices to communicate with other devices in the property.

The robotic devices further may include processor and storage capabilities. The robotic devices may include any suitable processing devices that enable the robotic devices to operate applications and perform the actions described throughout this disclosure. In addition, the robotic devices may include solid state electronic storage that enables the robotic devices to store applications, configuration data, collected sensor data, and/or any other type of information available to the robotic devices.

The robotic devices are associated with one or more charging stations. The charging stations may be located at predefined home base or reference locations in the property. The robotic devices may be configured to navigate to the charging stations after completion of tasks needed to be performed for the monitoring system 600. For instance, after completion of a monitoring operation or upon instruction by the control unit 610, the robotic devices may be configured to automatically fly to and land on one of the charging stations. In this regard, the robotic devices may automatically maintain a fully charged battery in a state in which the robotic devices are ready for use by the monitoring system 600.

The charging stations may be contact based charging stations and/or wireless charging stations. For contact based charging stations, the robotic devices may have readily accessible points of contact that the robotic devices are capable of positioning and mating with a corresponding contact on the charging station. For instance, a helicopter type robotic device may have an electronic contact on a portion of its landing gear that rests on and mates with an electronic pad of a charging station when the helicopter type robotic device lands on the charging station. The electronic contact on the robotic device may include a cover that opens to expose the electronic contact when the robotic device is charging and closes to cover and insulate the electronic contact when the robotic device is in operation.

For wireless charging stations, the robotic devices may charge through a wireless exchange of power. In these cases, the robotic devices need only locate themselves closely enough to the wireless charging stations for the wireless exchange of power to occur. In this regard, the positioning needed to land at a predefined home base or reference location in the property may be less precise than with a contact based charging station. Based on the robotic devices landing at a wireless charging station, the wireless charging station outputs a wireless signal that the robotic devices receive and convert to a power signal that charges a battery maintained on the robotic devices.

In some implementations, each of the robotic devices has a corresponding and assigned charging station such that the number of robotic devices equals the number of charging stations. In these implementations, the robotic devices always navigate to the specific charging station assigned to that robotic device. For instance, a first robotic device may always use a first charging station and a second robotic device may always use a second charging station.

In some examples, the robotic devices may share charging stations. For instance, the robotic devices may use one or more community charging stations that are capable of charging multiple robotic devices. The community charging station may be configured to charge multiple robotic devices in parallel. The community charging station may be configured to charge multiple robotic devices in serial such that the multiple robotic devices take turns charging and, when fully charged, return to a predefined home base or reference location in the property that is not associated with a charger. The number of community charging stations may be less than the number of robotic devices.

Also, the charging stations may not be assigned to specific robotic devices and may be capable of charging any of the robotic devices. In this regard, the robotic devices may use any suitable, unoccupied charging station when not in use. For instance, when one of the robotic devices has completed an operation or is in need of battery charge, the control unit 610 references a stored table of the occupancy status of each charging station and instructs the robotic device to navigate to the nearest charging station that is unoccupied.

The system 600 further includes one or more integrated security devices 680. The one or more integrated security devices may include any type of device used to provide alerts based on received sensor data. For instance, the one or more control units 610 may provide one or more alerts to the one or more integrated security input/output devices. Additionally, the one or more control units 610 may receive one or more sensor data from the sensors 620 and determine whether to provide an alert to the one or more integrated security input/output devices 680.

The sensors 620, the module 622, the camera 630, the thermostat 634, and the integrated security devices 680 communicate with the controller 612 over communication links 624, 626, 628, 632, 684, and 686. The communication links 624, 626, 628, 632, 684, and 686 may be a wired or wireless data pathway configured to transmit signals from the sensors 620, the module 622, the camera 630, the thermostat 634, and the integrated security devices 680 to the controller 612. The sensors 620, the module 622, the camera 630, the thermostat 634, and the integrated security devices 680 may continuously transmit sensed values to the controller 612, periodically transmit sensed values to the controller 612, or transmit sensed values to the controller 612 in response to a change in a sensed value.

The communication links 624, 626, 628, 632, 684, and 686 may include a local network. The sensors 620, the module 622, the camera 630, the thermostat 634, and the integrated security devices 680, and the controller 612 may exchange data and commands over the local network. The local network may include 802.11 "Wi-Fi" wireless Ethernet (e.g., using low-power Wi-Fi chipsets), Z-Wave, Zigbee, Bluetooth, "Homeplug" or other "Powerline" networks that operate over AC wiring, and a Category 5 (CAT5) or Category 6 (CAT6) wired Ethernet network. The local network may be a mesh network constructed based on the devices connected to the mesh network.

The monitoring application server 660 is an electronic device configured to provide monitoring services by exchanging electronic communications with the control unit 610, the one or more user devices 640 and 650, and the central alarm station server 670 over the network 605. For example, the monitoring application server 660 may be configured to monitor events (e.g., alarm events) generated by the control unit 610. In this example, the monitoring application server 660 may exchange electronic communications with the network module 614 included in the control unit 610 to receive information regarding events (e.g., alerts) detected by the control unit server 104a. The monitoring application server 660 also may receive information regarding events (e.g., alerts) from the one or more user devices 640 and 650.

In some examples, the monitoring application server 660 may route alert data received from the network module 614 or the one or more user devices 640 and 650 to the central alarm station server 670. For example, the monitoring application server 660 may transmit the alert data to the central alarm station server 670 over the network 605.

The monitoring application server 660 may store sensor and image data received from the monitoring system and perform analysis of sensor and image data received from the monitoring system. Based on the analysis, the monitoring application server 660 may communicate with and control aspects of the control unit 610 or the one or more user devices 640 and 650.

The central alarm station server 670 is an electronic device configured to provide alarm monitoring service by exchanging communications with the control unit 610, the one or more mobile devices 640 and 650, and the monitoring application server 660 over the network 605. For example, the central alarm station server 670 may be configured to monitor alerting events generated by the control unit 610. In this example, the central alarm station server 670 may exchange communications with the network module 614 included in the control unit 610 to receive information regarding alerting events detected by the control unit 610. The central alarm station server 670 also may receive information regarding alerting events from the one or more mobile devices 640 and 650 and/or the monitoring application server 660.

The central alarm station server 670 is connected to multiple terminals 672 and 674. The terminals 672 and 674 may be used by operators to process alerting events. For example, the central alarm station server 670 may route alerting data to the terminals 672 and 674 to enable an operator to process the alerting data. The terminals 672 and 674 may include general-purpose computers (e.g., desktop personal computers, workstations, or laptop computers) that are configured to receive alerting data from a server in the central alarm station server 670 and render a display of information based on the alerting data. For instance, the controller 612 may control the network module 614 to transmit, to the central alarm station server 670, alerting data indicating that a sensor 620 detected motion from a motion sensor via the sensors 620. The central alarm station server 670 may receive the alerting data and route the alerting data to the terminal 672 for processing by an operator associated with the terminal 672. The terminal 672 may render a display to the operator that includes information associated with the alerting event (e.g., the lock sensor data, the motion sensor data, the contact sensor data, etc.) and the operator may handle the alerting event based on the displayed information.

In some implementations, the terminals 672 and 674 may be mobile devices or devices designed for a specific function. Although FIG. 6 illustrates two terminals for brevity, actual implementations may include more (and, perhaps, many more) terminals.

The one or more user devices 640 and 650 are devices that host and display user interfaces. For instance, the user device 640 is a mobile device that hosts one or more native applications (e.g., the smart home application 642). The user device 640 may be a cellular phone or a non-cellular locally networked device with a display. The user device 640 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 640 may perform functions unrelated to the monitoring system, such as placing personal telephone calls, playing music, playing video, displaying pictures, browsing the Internet, maintaining an electronic calendar, etc.

The user device 640 includes a smart home application 642. The smart home application 642 refers to a software/firmware program running on the corresponding mobile device that enables the user interface and features described throughout. The user device 640 may load or install the smart home application 642 based on data received over a network or data received from local media. The smart home application 642 runs on mobile devices platforms, such as iPhone, iPod touch, Blackberry, Google Android, Windows Mobile, etc. The smart home application 642 enables the user device 640 to receive and process image and sensor data from the monitoring system.

The user device 650 may be a general-purpose computer (e.g., a desktop personal computer, a workstation, or a laptop computer) that is configured to communicate with the monitoring application server 660 and/or the control unit 610 over the network 605. The user device 650 may be configured to display a smart home user interface 652 that is generated by the user device 650 or generated by the monitoring application server 660. For example, the user device 650 may be configured to display a user interface (e.g., a web page) provided by the monitoring application server 660 that enables a user to perceive images captured by the camera 630 and/or reports related to the monitoring system. Although FIG. 6 illustrates two user devices for brevity, actual implementations may include more (and, perhaps, many more) or fewer user devices.

In some implementations, the one or more user devices 640 and 650 communicate with and receive monitoring system data from the control unit 610 using the communication link 638. For instance, the one or more user devices 640 and 650 may communicate with the control unit 610 using various local wireless protocols such as Wi-Fi, Bluetooth, Zwave, Zigbee, HomePlug (ethernet over powerline), or wired protocols such as Ethernet and USB, to connect the one or more user devices 640 and 650 to local security and automation equipment. The one or more user devices 640 and 650 may connect locally to the monitoring system and its sensors and other devices. The local connection may improve the speed of status and control communications because communicating through the network 605 with a remote server (e.g., the monitoring application server 660) may be significantly slower.

Although the one or more user devices 640 and 650 are shown as communicating with the control unit 610, the one or more user devices 640 and 650 may communicate directly with the sensors and other devices controlled by the control unit 610. In some implementations, the one or more user devices 640 and 650 replace the control unit 610 and perform the functions of the control unit 610 for local monitoring and long range/offsite communication.

In other implementations, the one or more user devices 640 and 650 receive monitoring system data captured by the control unit 610 through the network 605. The one or more user devices 640, 650 may receive the data from the control unit 610 through the network 605 or the monitoring application server 660 may relay data received from the control unit 610 to the one or more user devices 640 and 650 through the network 605. In this regard, the monitoring application server 660 may facilitate communication between the one or more user devices 640 and 650 and the monitoring system.

In some implementations, the one or more user devices 640 and 650 may be configured to switch whether the one or more user devices 640 and 650 communicate with the control unit 610 directly (e.g., through link 638) or through the monitoring application server 660 (e.g., through network 605) based on a location of the one or more user devices 640 and 650. For instance, when the one or more user devices 640 and 650 are located close to the control unit 610 and in range to communicate directly with the control unit 610, the one or more user devices 640 and 650 use direct communication. When the one or more user devices 640 and 650 are located far from the control unit 610 and not in range to communicate directly with the control unit 610, the one or more user devices 640 and 650 use communication through the monitoring application server 660.

Although the one or more user devices 640 and 650 are shown as being connected to the network 605, in some implementations, the one or more user devices 640 and 650 are not connected to the network 605. In these implementations, the one or more user devices 640 and 650 communicate directly with one or more of the monitoring system components and no network (e.g., Internet) connection or reliance on remote servers is needed.

In some implementations, the one or more user devices 640 and 650 are used in conjunction with only local sensors and/or local devices in a house. In these implementations, the system 600 only includes the one or more user devices 640 and 650, the sensors 620, the module 622, the camera 630, and the robotic devices. The one or more user devices 640 and 650 receive data directly from the sensors 620, the module 622, the camera 630, and the robotic devices and sends data directly to the sensors 620, the module 622, the camera 630, and the robotic devices. The one or more user devices 640, 650 provide the appropriate interfaces/processing to provide visual surveillance and reporting.

In other implementations, the system 600 further includes network 605 and the sensors 620, the module 622, the camera 630, the thermostat 634, and the robotic devices are configured to communicate sensor and image data to the one or more user devices 640 and 650 over network 605 (e.g., the Internet, cellular network, etc.). In yet another implementation, the sensors 620, the module 622, the camera 630, the thermostat 634, and the robotic devices (or a component, such as a bridge/router) are intelligent enough to change the communication pathway from a direct local pathway when the one or more user devices 640 and 650 are in close physical proximity to the sensors 620, the module 622, the camera 630, the thermostat 634, and the robotic devices to a pathway over network 605 when the one or more user devices 640 and 650 are farther from the sensors 620, the module 622, the camera 630, the thermostat 634, and the robotic devices. In some examples, the system leverages GPS information from the one or more user devices 640 and 650 to determine whether the one or more user devices 640 and 650 are close enough to the sensors 620, the module 622, the camera 630, the thermostat 634, and the robotic devices to use the direct local pathway or whether the one or more user devices 640 and 650 are far enough from the sensors 620, the module 622, the camera 630, the thermostat 634, and the robotic devices that the pathway over network 605 is required. In other examples, the system leverages status communications (e.g., pinging) between the one or more user devices 640 and 650 and the sensors 620, the module 622, the camera 630, the thermostat 634, and the robotic devices to determine whether communication using the direct local pathway is possible. If communication using the direct local pathway is possible, the one or more user devices 640 and 650 communicate with the sensors 620, the module 622, the camera 630, the thermostat 634, and the robotic devices using the direct local pathway. If communication using the direct local pathway is not possible, the one or more user devices 640 and 650 communicate with the sensors 620, the module 622, the camera 630, the thermostat 634, and the robotic devices using the pathway over network 605.

In some implementations, the system 600 provides end users with access to images captured by the camera 630 to aid in decision making. The system 600 may transmit the images captured by the camera 630 over a wireless WAN network to the user devices 640 and 650. Because transmission over a wireless WAN network may be relatively expensive, the system 600 uses several techniques to reduce costs while providing access to significant levels of useful visual information.

In some implementations, a state of the monitoring system and other events sensed by the monitoring system may be used to enable/disable video/image recording devices (e.g., the camera 630). In these implementations, the camera 630 may be set to capture images on a periodic basis when the alarm system is armed in an "Away" state, but set not to capture images when the alarm system is armed in a "Stay" state or disarmed. In addition, the camera 630 may be triggered to begin capturing images when the alarm system detects an event, such as an alarm event, a door-opening event for a door that leads to an area within a field of view of the camera 630, or motion in the area within the field of view of the camera 630. In other implementations, the camera 630 may capture images continuously, but the captured images may be stored or transmitted over a network when needed.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A computer-implemented method, comprising:
navigating, by an autonomous drone comprising an ultrasound transducer, to a location where a person is located during an alarm event at a property;
in response to navigating to the location, performing, by the autonomous drone, one or more ultrasound scans of the person by moving in a proximity of the person and directing sound waves of the ultrasound transducer over different portions of the person's body;
providing, by the autonomous drone and to a trained model, first data indicating the one or more ultrasound scans of the person;
obtaining, by the autonomous drone, second data indicating a health condition predicted by the trained model, wherein the health condition is about the person and the trained model predicts the health condition based on the first data indicating the one or more ultrasound scans of the person; and
providing, by the autonomous drone, the second data indicating the health condition of the person for output.

2. The method of claim 1, further comprising:
generating, by the autonomous drone, a map of the property; and
providing the first data indicating the one or more ultrasound scans of the person comprises providing, to the trained model, data indicating the map of the property.

3. The method of claim 1, wherein the health condition indicates that the person is likely injured.

4. The method of claim 1, further comprising:
obtaining, by the autonomous drone, sensor data collected by one or more sensors located in the property;
providing, by the autonomous drone, the sensor data to a second trained model; and
obtaining, by the autonomous drone, data indicating the location of the person that was predicted by the second trained model based on the sensor data.

5. The method of claim 1, wherein:
the autonomous drone comprises a microphone;
the method further comprises:
collecting, by the autonomous drone, audio data collected by the microphone at the location where the person is located during the alarm event at the property; and
determining, by the autonomous drone, whether the person is alive based on the audio data.

6. The method of claim 1, further comprising:
   determining, by the autonomous drone, whether the person is injured based on the health condition that was predicted by the trained model; and
   providing, by the autonomous drone and for output to a device located outside of the property, an indication as to whether the person is injured.

7. The method of claim 6, wherein the device located outside the property comprises a device associated with a first responder.

8. A system comprising:
   one or more computing devices; and
   one or more non-transitory computer-readable devices storing instructions that, when executed by the one or more computing devices, cause the one or more computing devices to perform operations comprising:
      navigating, by an autonomous drone comprising an ultrasound transducer, to a location where a person is located during an alarm event at a property;
      in response to navigating to the location, performing, by the autonomous drone, one or more ultrasound scans of the person by moving in a proximity of the person and directing sound waves of the ultrasound transducer over different portions of the person's body;
      providing, by the autonomous drone and to a trained model, first data indicating the one or more ultrasound scans of the person;
      obtaining, by the autonomous drone, second data indicating a health condition predicted by the trained model, wherein the health condition is about the person and the trained model predicts the health condition based on the first data indicating the one or more ultrasound scans of the person; and
      providing, by the autonomous drone, the second data indicating the health condition of the person for output.

9. The system of claim 8, wherein the operations further comprise:
   generating, by the autonomous drone, a map of the property; and
   providing the first data indicating the one or more ultrasound scans of the person comprises providing, to the trained model, data indicating the map of the property.

10. The system of claim 8, wherein the health condition indicates that the person is likely injured.

11. The system of claim 8, wherein the operations further comprise:
   obtaining, by the autonomous drone, sensor data collected by one or more sensors located in the property;
   providing, by the autonomous drone, the sensor data to a second trained model; and
   obtaining, by the autonomous drone, data indicating the location of the person that was predicted by the second trained model based on the sensor data.

12. The system of claim 8, wherein:
   the autonomous drone comprises a microphone;
   the operations further comprise:
      collecting, by the autonomous drone, audio data collected by the microphone at the location where the person is located during the alarm event at the property; and
      determining, by the autonomous drone, whether the person is alive based on the audio data.

13. The system of claim 8, wherein the operations further comprise:
   determining, by the autonomous drone, whether the person is injured based on the health condition that was predicted by the trained model; and
   providing, by the autonomous drone and for output to a device located outside of the property, an indication as to whether the person is injured.

14. The system of claim 13, wherein the device located outside the property comprises a device associated with a first responder.

15. At least one non-transitory computer-readable storage device storing instructions that, when executed by one or more processors, cause the one or more processors to perform operations comprising:
   navigating, by an autonomous drone comprising an ultrasound transducer, to a location where a person is located during an alarm event at a property;
   in response to navigating to the location, performing, by the autonomous drone, one or more ultrasound scans of the person by moving in a proximity of the person and directing sound waves of the ultrasound transducer over different portions of the person's body;
   providing, by the autonomous drone and to a trained model, first data indicating the one or more ultrasound scans of the person;
   obtaining, by the autonomous drone, second data indicating a health condition predicted by the trained model, wherein the health condition is about the person and the trained model predicts the health condition based on the first data indicating the one or more ultrasound scans of the person; and
   providing, by the autonomous drone, the second data indicating the health condition of the person for output.

16. The non-transitory computer-readable storage device of claim 15, wherein the operations further comprise:
   generating, by the autonomous drone, a map of the property; and
   providing the first data indicating the one or more ultrasound scans of the person comprises providing, to the trained model, data indicating the map of the property.

17. The non-transitory computer-readable storage device of claim 15, wherein the health condition indicates that the person is likely injured.

18. The non-transitory computer-readable storage device of claim 15, wherein the operations further comprise:
   obtaining, by the autonomous drone, sensor data collected by one or more sensors located in the property;
   providing, by the autonomous drone, the sensor data to a second trained model; and
   obtaining, by the autonomous drone, data indicating the location of the person that was predicted by the second trained model based on the sensor data.

19. The non-transitory computer-readable storage device of claim 15, wherein:
   the autonomous drone comprises a microphone;
   the operations further comprise:
      collecting, by the autonomous drone, audio data collected by the microphone at the location where the person is located during the alarm event at the property; and
      determining, by the autonomous drone, whether the person is alive based on the audio data.

20. The non-transitory computer-readable storage device of claim 15, wherein the operations further comprise:
   determining, by the autonomous drone, whether the person is injured based on the health condition that was predicted by the trained model; and providing, by the autonomous drone and for output to a device located outside of the property, an indication as to whether the person is injured.

\* \* \* \* \*